(12) United States Patent
Winter

(10) Patent No.: US 6,376,458 B1
(45) Date of Patent: Apr. 23, 2002

(54) UTILIZATION OF CYCLIC COMPOUNDS AS PERFUMING INGREDIENTS

(75) Inventor: Beat Winter, Bernex (CH)

(73) Assignee: Firmewich SA, Geneva (CH)

( * ) Notice: Subject to any disclaimer, the term of this patent is extended or adjusted under 35 U.S.C. 154(b) by 0 days.

(21) Appl. No.: 09/567,891

(22) Filed: May 10, 2000

(30) Foreign Application Priority Data

May 19, 1999 (CH) ................................................ 0939/99

(51) Int. Cl.$^7$ .................................................. A61K 7/46

(52) U.S. Cl. .............................. 512/26; 512/8; 568/446

(58) Field of Search ........................ 512/26, 8; 568/446

(56) References Cited

U.S. PATENT DOCUMENTS 5,552,379 A * 9/1996 Winter et al. .................. 512/12

FOREIGN PATENT DOCUMENTS

EP          0 685 444      * 12/1995

OTHER PUBLICATIONS

G. Ohloff et al., "Conformationally Controlled Odor Perception in 'Steroid–type' Scent Molecules", *Helvetica Chimica Acta*, vol. 66, Fasc. 5, p. 1343–1354 (1983).*

* cited by examiner

*Primary Examiner*—Jill Warden
*Assistant Examiner*—Monique T. Cole
(74) *Attorney, Agent, or Firm*—Winston & Strawn

(57) ABSTRACT

A compound of formula

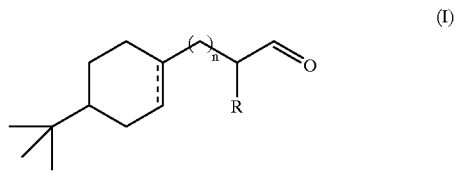

(I)

wherein either the dotted line indicates the location of a double bond, n is equal to 1 and R represents a hydrogen atom or a methyl radical, or the dotted line indicates the location of a single bond, n is equal to 0 and R represents a hydrogen atom, is useful as a perfuming ingredient for the preparation of perfuming compositions and perfumed products, to which it imparts odor notes of the lily of the valley type.

4 Claims, No Drawings

UTILIZATION OF CYCLIC COMPOUNDS AS PERFUMING INGREDIENTS

BRIEF SUMMARY OF THE INVENTION

The present invention relates to the field of perfumery. It concerns more particularly the use as a perfuming ingredient of a compound of formula

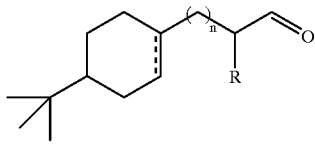

(I)

wherein either the dotted line indicates the location of a double bond, n is equal to 1 and R represents a hydrogen atom or a methyl radical, or the dotted line indicates the location of a single bond, n is equal to 0 and R represents a hydrogen atom.

The cyclic compounds of formula (I) possess very useful and appreciated odor properties. Therefore, they can be useful for the preparation of perfumes, perfuming compositions and perfumed products. They are employed in order to confer odor notes of the lily of the valley type.

BACKGROUND OF THE INVENTION

The structure of the compound of formula (I) wherein the dotted line indicates the location of a single bond, n is equal to 0 and R represents a hydrogen atom, namely (4-tert-butyl-1-cyclohexyl)acetaldehyde, is known. In fact, this compound is cited by G. Ohloff et al. as a synthesis intermediate in Helvetica Chimica Acta (1983), 66(5), 1343–1354. However, said reference does not contain any description of the odor of (4-tert-butyl-1-cyclohexyl)acetaldehyde. The organoleptic properties of some compounds synthesized are described in this document, but the described odors are typical of those of compounds of the steroid type, while the compound of the invention possesses a very natural odor, which is reminiscent of that of Lilial® [3-(4-tert-butylphenyl)-2-methylpropanal), and which presents, besides, a nice citrus connotation. Moreover, (4-tert-butyl-1-cyclohexyl) acetaldehyde possesses in its bottom note, a very original and appreciated odor of the melon, aqueous, mandarin-fresh type.

The compounds of formula (I), wherein the dotted line indicates the location of a double bond, n is equal to 1 and R represents a hydrogen atom or a methyl radical, namely 3-(4-tert-butyl-1-cyclohexen-1-yl)propanal and 3-(4-tert-butyl-1-cyclohexen-1-yl)2-methylpropanal are novel compounds. The known compounds having the closest structure to those two, are respectively Bourgeonal® [3-(4-tert-butylphenyl)propanal] and Lilial® [3-(4-tert-butylphenyl)-2-methylpropanal]. Besides, European patent application EP 685 444 discloses the odor properties of some aldehydes, the structure of which is also close to that of the compounds of the invention. However, contrary to the compounds of the invention, these known aldehydes possess an aromatic ring. Despite the large number of known aldehydes having a structure which is close to that of the compounds of formula (I), nothing in the literature suggests that the compounds of formula (I) according to the invention would be susceptible of being interesting from an olfactory point of view.

DETAILED DESCRIPTION OF THE INVENTION

Surprisingly, we have now been able to establish that the compounds of formula (I) possess very interesting odor properties, providing useful nuances to the perfumer's palette. These compounds possess an odor which is reminiscent of that of Lilial® and Bourgeonal®, but which is also fresher, more floral and less fatty than that of the known products.

The invention is thus related to a method to confer, improve, enhance or modify the odor properties of a perfuming composition or a perfumed product, which method comprises adding a compound of formula

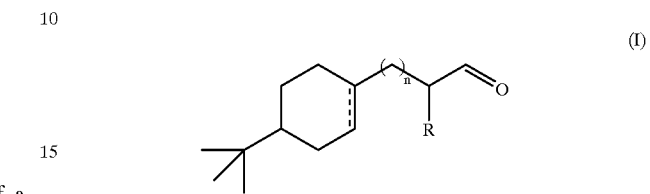

(I)

wherein either the dotted line indicates the location of a double bond, n is equal to 1 and R represents a hydrogen atom or a methyl radical, or the dotted line indicates the location of a single bond, n is equal to 0 and R represents a hydrogen atom, as a perfuming ingredient to said composition or product.

The compounds of the invention thus make it possible to confer, improve, enhance or modify the odor of consumer products, as well as of perfuming bases or concentrates. In other words, they can impart to the latter their characteristic odor, as the case may be modifying and/or improving the original odor properties of the products and compositions in which they are incorporated. These products thus become more appealing to the consumer and have an enhanced odor impact.

In particular, 3-(4-tert-butyl-1-cyclohexen-1-yl)-2-methylpropanal presents an odor with a top note of the lily of the valley, almost white flower, freesia type. Its odor is mild and very pleasant.

3-(4-Tert-butyl-1-cyclohexen-1-yl)propanal is a preferred compound according to the invention. The latter presents an odor of the aldehydic, flowery-lily of the valley, fatty type with a Lilial®/Bourgeonal® connotation, but its odor is definitely more floral, more white flower than that of Lilial®. It is also more powerful than the latter, more substantive on the linen, which property presents a distinct advantage for the perfuming of products such as detergents and fabric softeners. Moreover, the odor of this preferred compound of the invention has a surprising slight anisic tone, providing thus a novel odor nuance to the perfumer's palette.

The compounds of the invention can suit an utilization in fine perfumery, in perfumes, colognes, or after-shave lotions, as well as any current use in perfumery such as the perfuming of soaps, shower or bath gels, hygiene products, hair-care products such as shampoos, as well as body deodorants and air fresheners, or yet cosmetic preparations.

The compounds (I) can also be used in applications such as liquid or solid detergents for textile treatment, fabric softeners, or yet detergent compositions or cleaning products for dishes or varied surfaces, for a domestic as well as an industrial use.

In these applications, the compounds of the invention can be used alone as well as mixed with other perfuming ingredients, solvents or additives commonly used in perfumery. The nature and variety of these co-ingredients does not require a more detailed description here, which would not be exhaustive anyway. In fact, a person skilled in the art having a general knowledge, is able to choose them according to the nature of the product that has to be perfumed and the olfactory effect sought.

These perfuming co-ingredients belong to varied chemical groups such as alcohols, aldehydes, ketones, esters, ethers, acetates, nitrites, terpenic hydrocarbons, herterocyclic nitrogen- or sulfur-containing compounds, as well as essential oils of natural or synthetic origin. Many of these ingredients are listed in reference texts such as S. Arctander, Perfume and Flavor Chemicals, 1969, Montclair, N.J., USA or more recent versions thereof, or in other similar books.

The proportions in which the compounds according to the invention can be incorporated in the different products mentioned above, vary in a large range of values. These values depend on the nature of the article or product that has to be perfumed, and on the olfactory effect sought, as well as on the nature of the co-ingredients in a given composition when the compounds of the invention are used in admixture with perfuming co-ingredients, solvents or additives of current use in the art.

For instance, typical concentrations from about 4 to 10% by weight, or even 20% or more by weight of the compound (I) of the invention, with respect to the weight of the composition in which it is incorporated can be used. Much lower concentrations than these can be used when these compounds are directly applied for perfuming the consumer products mentioned above.

The compounds of formula (I) wherein the dotted line indicates the location of a double bond, n is equal to 1 and R represents a hydrogen atom or a methyl radical can be prepared by a three, respectively five-step process, starting form 4-tert-butyl-cyclohexanone. The latter, in the presence of the classical reactant 2-(2-bromoethyl)-1,3-dioxalane, makes it possible to obtain, after a Grignard reaction followed by a dehydration reaction and a hydrolysis, in standard reaction conditions, 3-(4-tert-butyl-1-cyclohexen-1-yl) propanal. The intermediates of this synthesis, namely 4-tert-butyl-1-[2-(1,3-dioxalan-2-yl)ethyl]-1-cyclohexanol at the end of the first step, and a mixture of 2-[2-(4-tert-butyl-1-cyclohexen-1-yl)ethyl]-1,3-dioxalane and 2-[2-(4-tert-1-butyl-1-cyclohexylidene)ethyl] at the end of the second step, are novel compounds. The final product of the synthesis, namely 3-(4-tert-butyl-1-cyclohexen-1-yl)propanal, after a reaction of the Mannich type, followed by a selective hydrogenation, leads to 3-(4-tert-butyl-1-cyclohexen-1-yl)-2-methylpropanal, another compound of the invention. Finally the compound of formula (I) wherein the dotted line indicates the location of a single bond, n is equal to 0 and R represents a hydrogen atom, namely (4-tert-butyl-1-cyclohexyl)acetaldehyde, is prepared in a one step reaction by lithium aluminum hydride reduction of methyl-4-tert-butyl-1-cyclohexylideneacetate. The different steps of these syntheses will be described in a more detailed manner in the examples hereafter.

The invention will now be described in greater detail in the following examples, wherein the temperatures are indicated in degrees centigrade and the abbreviations have the usual meaning in the art.

EXAMPLE 1

Preparation of 3-(4-tert-butyl-1-cyclohexen-1-yl) propanal i) 4-tert-butyl-1-[2-(1,3-dioxalan-2-yl)ethyl]-1-cyclohexanol There was added dropwise a solution of 58 ml (0.47 mol) 2-(2-bromoethyl)-1,3-dioxalane (origin: Fluka) in 350 ml of tetrahydrofurane (THF), to 12.6 g (0.52 mol) of a suspension under stirring of magnesium turnings in 20 ml of THF at room temperature. The reaction was initialized by adding a little bit of iodine and methyl iodide. With the help of a water bath, the temperature was maintained at 30° during the addition. The reaction mixture was then maintained under stirring at room temperature during 2 h. Then, a solution of 50 g (0.31 mol) of 4-tert-butyl-cyclohexanone (origin: Fluka) in 125 ml THF was added dropwise at a temperature below 30°. The mixture was stirred at room temperature during 1 h 30 and then poured on a mixture of ether, ice and ammonium chloride. The organic phase was washed 3 times with the help of brine, then dried over $Na_2SO_4$ and concentrated to obtain 85.4 g of 4-tert-butyl-1-[2-(1,3-dioxalan-2-yl)ethyl]-1-cyclohexanol in the form of an oil, with a purity of 90% (trans/cis=1:2, yield: 95%). This compound was used as such for the next steps.

Analytical data: (major isomer)

IR(neat): 3440, 2960, 2930, 2860, 1470, 1440, 1400, 1385, 1360, 1260, 1140, 1035, 940 $cm^{-1}$.

NMR($^1$H, 360 MHz, $CDCl_3$): 4.88(t, J=4, 1H); 3.98(m, 2H); 3.85(m, 1H); 1.87–1.00(m, 13H); 1.71(OH); 0.86(s, 9H).

NMR($^{13}$C, 90.5 MHz, $CDCl_3$): 104.8(d); 69.8(s); 64.9 (2t); 48.0(d); 38.7(t); 37.5(t); 27.5(t); 24.4(t); 22,5(2t).

MS: 256($M^+$, 0.5), 194(1), 185(1), 157(48), 139(6), 113 (7), 102(21), 95(23), 86(24), 73(100), 57(35), 41(24), 29(15).

ii) 2-[2-(4-tert-butyl-1-cyclohexen-1-yl)ethyl]-1,3-dioxalane

There were added dropwise 8.6 ml (93.0 mmol, 1.5 eq) of phosphorus oxychloride ($POCl_3$) (origin: Aldrich) to a stirred solution of 17.8 g (62 mmol) of the hydroxy-acetal obtained under i) in 75 ml of pyridine at a temperature comprised between 0 and 4° (ice-water bath). After 15 min, the cooling bath was removed and the mixture was allowed to reach room temperature. At this temperature, a slight exothermic reaction occurred during which the temperature increased to 38° in 1 h. The reaction mixture was maintained at room temperature during 1 more hour, and then cooled again to 0–4°. Cautiously (exothermic reaction), ice and water were added, followed by ether and the mixture was stirred during 1 h at room temperature. It was then diluted with ether and water. The organic phase was washed with aq. sat. $NaHCO$ and brine (2×), dried ($K_2CO_3$) and concentrated to give 15.8 g of an oil. A bulb to bulb distillation (10 Pa, oven temperature 130°) allowed to obtain 12.2 g of a mixture of 2-[2-(4-tert-butyl-1-cyclohexen-1-yl)ethyl]-1,3-dioxalane and its isomer 2-[2-(4-tert-butyl-1-cyclohexylidene)ethyl]-1,3-dioxalane in a 9:1 ratio, with a purity of 94% (yield: 78%).

Analytical data:

IR(neat): 2960, 2870, 1660, 1640, 1460, 1435, 1400, 1380, 1355, 1135, 1030, 935 $cm^{-1}$.

NMR($^1$H, 360 MHz, $CDCl_3$): 5.43(m, 1H); 4.86(t, J=5, 1H); 3.96(m, 2H); 3.85(m, 2H); 2.1–1.95(m, 5H); 1.85–1.70 (m, 4H); 1.28–1.10(m, 2H); 0.86(s, 9H).

NMR($^{13}$C, 90.5 MHz, $CDCl_3$); 136.7(s); 121.2(d); 104.4 (d); 64.8(2t); 44.2(d); 32.2(s+t); 31.7(t); 29.9(t); 27.2(q); 26.8(t); 24.3(t).

MS: 238($M^+$, 1), 223(1), 209(6), 176(9), 161(4), 119(13), 99(39), 86(100), 73(37), 57(22), 45(16), 41(18), 29(9).

iii) 3-(4-tert-butyl-1-cyclohexen-1-yl)propanal

There were added to a solution of 25.6 g (0.10 mol) of the dioxalane obtained under ii) in 390 ml of acetone and 130 ml of water, 2.2 ml of conc. HCl. The mixture was heated to reflux (internal temperature 71°) during 22 h. Once cooled, the mixture was diluted with ether and sat. aq. NaHCO$_3$. The organic phase was washed 2× with brine, dried over Na$_2$SO$_4$ and concentrated to give 21.3 g of a yellow liquid. After a distillation under vacuum (15 cm, "Widmer type column, 10 Pa), there were obtained 16.2 g of 3-(4-tert-butyl-1-cyclohexen-1-yl)propanal in the form of a colorless oil, with a purity of 95% (yield: 75%).

Analytical data

B.P.: 52–64° (10 Pa)

IR(neat): 2960, 2820, 2700, 1720, 1460, 1430, 1385, 1355, 1240, 1225, 910 cm$^{-1}$.

NMR($^1$H, 360 MHz, CDCl$_3$): 9.76(t, J=2.1H); 5.42(m, 1H); 2.52(m, 2H); 2.28(t, J=8, 2H); 2.05–1.90(m, 3H); 1.85–1.70(m, 2H); 1.25–1.10(m, 2H); 0.86(s, 9H).

NMR($^{13}$C, 90.5 MHz, CDCl$_3$): 202.8(d); 135.5(s); 122.1 (d); 44.0(d); 41.9(t); 32.2(s); 29.9(t); 29.7(t); 27.2(q); 26.7 (t); 24.1(t).

MS: 194(M$^+$, 7), 179(1), 176(2), 161(4), 150(9), 137(9), 120(22), 109(12), 94(41), 91(45), 79(34), 67(31), 57(100), 41(71), 29(38).

EXAMPLE 2

Preparation of 3-(4-tert-butyl-1-cyclohexen-1-yl)-2-methylpropanal

This compound was prepared starting from 3-(4-tert-butyl-1-cyclohexen-1-yl)propanal obtained as described in Example 1.

i) 2-[(4-tert-butyl-1-cyclohexen-1-yl)methyl]-2-propenal

There were added dropwise 3.6 ml (21 mmol) of dibutylamine to a mixture under stirring of 3.67 g (17.3 mmol) of 3-(4-tert-butyl-1-cyclohexen-1-yl)propanal and 2.94 ml (39 mmol) of 36% aq. formaldehyde heated to reflux (110°) .There was observed the formation of a yellow emulsion. The reaction mixture was heated to reflux during 1 h. Once cooled, the mixture was diluted with ether and sat. aq. NH$_4$Cl. The organic phase was washed with brine (2×), dried over Na$_2$SO$_4$ and concentrated to obtain 5.38 g of a yellow-brown liquid. After a distillation on a bulb to bulb oven (water exhauster (ca 13×10$^2$ Pa), oven temperature 200°), 2.6 g of a yellow oil with a purity of 80% were obtained. A chromatography on an SiO$_2$ column (150 g) with a 9:1 mixture of cyclohexane-ether as elution agent, gave 1.72 g of a yellow liquid, 96% pure. Finally, after a distillation on a bulb to bulb oven (18 Pa, oven temperature 100°), there were obtained 1.50 g of 2-[(4-tert-butyl-1-cyclohexen-1-yl)methyl]-2-propenal with a purity of 99% (yield: 42%).

Analytical data

IR(neat): 2960, 2910, 2830, 2680, 1685, 1615, 1460, 1425, 1355, 1240, 950, 940 cm$^{-1}$.

NMR($^1$H, 360 MHz, CDCl$_3$): 9.58(s, 1H); 6.23(d, J=0.5, 1H); 6.05(d, J=0.5, 1H); 5.45(m, 1H); 2.88(s, 2H); 2.10–1.90(m, 3H); 1.85–1.70(m, 2H); 1.28–1.08(m, 2H); 0.86(s, 9H).

NMR($^{13}$C, 90.5 MHz, CDCl$_3$): 194.4(d); 148.4(s); 134.8 (t); 134.0(s); 124.3(d); 44.0(d); 35.2(t); 32.2(s); 29.6(t); 27.2(q); 26.9(t); 24.2(t).

MS: 206(M$^+$, 26), 191(3), 177(4), 149(19), 131(22), 122 (29), 108(26), 91(50), 79(72), 57(96), 41(100), 29(50).

ii) 3-(4-tert-butyl-1-cyclohexen-1-yl)-2-methylpropanal

There were added 50 mg of 5% Pd-C and 50 mg (0.6 mmol) of sodium acetate to a solution of 1.13 g (5.4 mmol) of 2-[(4-tert-butyl-1-cyclohexen-1-yl)methyl]-2-propenal obtained under i). The mixture was vigorously stirred under an H$_2$ atmosphere (1 atm) at room temperature during 1 h. The catalyst was filtered and the solution was rinsed and concentrated to get 1.08 g of a colorless liquid. A distillation on a bulb to bulb oven (15 Pa, oven temperature 110°) allowed to obtain 1.03 g of 3-(4-tert-butyl-1-cyclohexen-1-yl)-2-methylpropanal in the form of a colorless oil with a purity of 99% (yield: 92%).

Analytical data:

IR(neat): 2960, 2860, 2820, 2700, 1720, 1460, 1445, 1385, 1360, 1240, 1225, 910 cm$^{-1}$.

NMR($^1$H, 360 MHz, CDCl$_3$): 9.62 and 9.61(2d, J=2, 1H); 5.45(m, 1H); 2.51(m, 1H); 2.48(m, 1H); 2.06–1.90(m, 4H); 1.86–1.70(m, 2H); 1.27–1.10(m, 2H); 1.04 and 1.03(2d, J=7, 3H); 0.86(2s, 9H).

NMR($^{13}$C, 90.5 MHz, CDCl$_3$); 205.3(d), 134.0(s); 124.2 (d); 44.4(d); 44.0(d); 38.8(t); 32.2(s); 29.7(t); 27.2(q); 26.9 (t); 24.2(t); 13.5 and 13,2(q).

MS: 208(M$^+$, 7), 193(1), 190(4), 179(6), 166(17), 151 (11), 133(12), 123(14), 109(16), 94(36), 91(36), 81(51), 79(40), 67(30), 57(100), 41(78), 29(43).

EXAMPLE 3

Preparation of (4-tert-butyl-1-cyclohexyl)acetaldehyde

This compound was prepared starting from methyl-4-tert-butyl-1-cyclohexylideneacetate: The synthesis of the latter is described in the literature by H. House et al. in J. Org. Chem., 1966, 31, 3128. This article is hereby included by reference.

A 6000 ml four necked round bottom flask was purged with nitrogen. There were charged 30.0 g (0.783 mol) of LiALH$_4$ under slow stirring. Dropwise, 400 ml of anhydrous THF were added over 30 min. An exothermic reaction occurred, and the gray suspension was cooled to 0° (isopropanol/CO$_2$ bath). A 15% solution of LiAlH4 in toluene/THF (37.7 g, 0.149 mol) was added in one portion, followed by the dropwise addition of a solution of methyl-4-tert-butyl-1-cyclohexylideneacetate (378.5 g, 94.1% pure, 1.694 mol) in 700 ml of dry THF. The addition took 5 h 40 min, while the internal temperature was maintained below 10°. A gas chromatography showed that no starting ester remained. The mixture was then stirred overnight at room temperature.

The hydrolysis was done at 2° by careful and very slow addition of 68.0 g of water, followed by 68.0 g of 15% aq. NaOH and finally a second portion of 210.0 g of water under vigorous stirring. The reaction was very exothermic. The mixture was stirred at room temperature overnight. The resulting white suspension was filtered through a Nutsche and filter-aid (solkafloc) and thoroughly rinsed with THF. The filtrate was concentrated under reduced pressure to afford 334.5 g (102%) of crude product.

The crude product was distilled through a 20 cm Vigreux column, affording 14 fractions. The distillation fractions were pooled and redistilled through a 35 cm Fischer Spaltrohr column, affording 29 fractions. A mixture of isomers of 4-tert-butyl-1-cyclohexyl)acetaldehyde was isolated (35.8% of trans isomer and 61.3% of cis isomer).

Analytical data:

NMR($^1$H, 360 MHz, CDCl$_3$): 9.75(m, 1H); 2.48–2.25(m, 2H); 1.80(m, 2H); 1.55(m, 4H); 1.18–0.90(m, 4H); 0.85(s, 9H).

NMR($^{13}$C, 90.5 MHz, CDCl$_3$): trans isomer: 203.0(d); 51.3(t); 47.7(d); 32.9(d); 33.7(2t); 32.4(s); 27.5(3q); 27.1(2t) cis isomer: 203.2(d); 48.2(d); 45.7(t); 32.6(s); 30.6(2t); 27.4(3q); 27.2(d); 21.6(2t).

MS: trans isomer: 182(M$^+$, <1), 149(6), 138(14), 125(24), 108(14), 81(36), 80(28), 67(26), 57(100), 56(38), 55(26), 41(62), 39(22), 29(38).

MS: cis isomer: (no M⁺), 149(6), 138(28), 125(14), 108(16), 81(38), 80(40), 67(24), 57(100), 56(26), 55(20), 41(36), 29(17).

EXAMPLE 4
Preparation of a Perfuming Composition for a Fabric Softener

A base perfuming composition for a fabric softener was prepared by admixing the following ingredients:

| Ingredients | Parts by weight |
| --- | --- |
| Benzyl acetate | 300 |
| 10% * cis-3-Hexenol acetate | 50 |
| 50% * Cinnamic alcohol | 100 |
| 10% * Anisic aldehyde | 150 |
| 10% * C12 aldehyde | 50 |
| Hexylcinnamic aldehyde | 550 |
| Amyl allyl glycolate | 20 |
| Methyl anthranilate | 10 |
| Bacdanol ®[1] | 60 |
| 10% * α-Damascone | 50 |
| Dihydromyrcenol[2] | 200 |
| Diphenyloxide | 50 |
| Eugenol | 50 |
| 10% * Geranyl nitrile[3] | 150 |
| Habanolide ®[4] | 360 |
| Phenethylol | 500 |
| 10% * cis-3-Hexenol dist. | 10 |
| Verdyl propionate[5] | 50 |
| Rosinol cryst.[6] | 20 |
| Amyl salicylate | 600 |
| Terpineol | 500 |
| Tubereuse abs. | 40 |
| γ-Undecalactone | 40 |
| Verdox ®[7] | 90 |
| Total | 4000 |

* in dipropyleneglycol
[1])2-ethyl-4-(2,2,3-trimethyl-3-cyclopenten-1-yl)-2-buten-1-ol; origin: International Flavors and Fragrances, USA
[2])origin: International Flavors and Fragrances, USA
[3])3,7-dimethyl-2,6-octatrienenitrile; origin: Firmenich SA, Geneva, Switzerland
[4])pentadecenolide; origin: Firmenich SA, Geneva, Switzerland
[5])origin: Givaudan-Roure SA, Vernier, Switzerland
[6])2,2,2-trichloro-1-phenylethyl acetate; origin: Firmenich SA, Geneva, Switzerland
[7])2-tert-butyl-1-cyclohexyl acetate; origin: International Flavors and Fragrances, USA When 400 parts by weight of 3-(4-tert-butyl-1-cyclohexen-1-yl)propanal were added to this composition, the latter acquired a distinctly elegant and sparkling lily of the valley white flower connotation. Moreover, 3-(4-tert-butyl-1-cyclohexen-1-yl)propanal conferred to the base composition more power to its top and bottom notes.

EXAMPLE 5
Preparation of a Perfuming Composition for a Cologne for Women

A base perfuming composition was prepared by admixing the following ingredients:

| Ingredients | Parts by weight |
| --- | --- |
| 10% * Phenylacetic aldehyde | 20 |
| Ambrettolide | 40 |
| Dihydro-β-ionone[1] | 350 |
| 3-(4-Methoxyphenyl)-2-methylpropanal[2] | 60 |
| 7-Methyl-(2H, 4H)-1,5-benzodioxepin-3-one[3] | 80 |
| Citronellol | 300 |
| 10% * Cyclogalbanate[4] | 200 |
| γ-Decalactone | 20 |
| Dimetol ®[5] | 20 |
| 10% * Ethylvanilline | 100 |
| Eugenol | 80 |
| Exaltolide ®[6] | 300 |
| Galaxolide ®[7] | 2300 |
| Hedione ® HC[8] | 700 |
| Heliopropanal[9] | 270 |
| 10% * Indol | 150 |
| Iso E super[10] | 1300 |
| Linalol | 270 |
| 10% * 2,6-Dimethyl-5-heptanal | 50 |
| Muscenone δ[11] | 250 |
| Phenethylol | 70 |
| β-Ionone | 20 |
| 10% * Zestover[12] | 50 |
| Total | 7000 |

* in dipropyleneglycol
[1])4-(2,2,6-trimethyl-2-cyclohexen-1-yl)-2-butanone; origin: Firmenich SA, Geneva, Switzerland
[2])origin: Firmenich SA, Geneva, Switzerland
[3])origin: Firmenich SA, Geneva, Switzerland
[4])allyl (cyclohexyloxy) acetate; origin: Dragoco, Holzminden, Allemagne
[5])2,6-dimethyl-2-heptanol; origin: Givaudan-Roure, Vernier, Switzerland
[6])pentadecenolide; origin: Firmenich SA, Geneva, Switzerland
[7])1,3,4,6,7,8-hexahydro-4,6,6,7,8,8-hexamethyl-cyclopenta-g-2-benzopyrane; origin: International Flavors and Fragrances, USA
[8])methyl dihydrojasmonate with a high cis isomer content; origin: Firmenich SA, Geneva, Switzerland
[9])3-(1,3-benzodioxol-5-yl)-2-methylpropanal; origin: Firmenich SA, Geneva, Switzerland
[10])1-(octahydro-2,3,8,8-tetramethyl-2-naphtalenyl)-1-ethanone; origin: International Flavors and Fragrances, USA
[11])3-methyl-cyclopentadecenone; origin: Firmenich SA, Geneva, Switzerland
[12])2,4-dimethyl-3-cyclohexene-1-carbaldehyde; origin: Firmenich SA, Geneva, Switzerland The addition of 300 parts by weight of 3-(4-tert-butyl-1-cyclohexen-1-yl)propanal imparted to this base perfuming composition an almost aqueous very nice floral-transparent note and accompanied in a wonderful manner the green notes of the base composition, rendering them more sophisticated. The novel composition possessed much more sparkle in the top note, and the substantivity of the floral note was enhanced during the evaporation.

The addition of 300 parts by weight of 3-(4-tert-butyl-1-cyclohexen-1-yl)-2-methyl-propanal imparted to the base perfume a lily of the valley-lilac connotation more metallic than in the previous case.

EXAMPLE 6
Comparative Example of Substantivity on Linen

A substantivity test was carried out on linen, by comparing the performance of 3-(4-tert-butyl-1-cylohexen-1-yl) propanal with that of its known analogue, namely 3-(4-tert-butyl-1-phenyl)-2-methylpropanal, or Lilial®, on various types of textiles (cotton, Nylon®, acrylic or mixtures thereof).

To this end, there were added to a standard, non perfumed fabric softener, respectively 0.1% of 3-(4-tert-butyl-1-cyclohexen-1-yl)propanal (sample A) and 0.1% of 3-(4-tert-butyl-1-phenyl)-2-methylpropanal (sample B) in order to prepare two samples of a perfumed fabric softener.

Four batches of standard textiles containing respectively cotton, Nylon®, acrylic fibers and finally a mixture of the three textiles were treated separately in four washing machines. The batches of textiles thus treated were evaluated on a blind test by a panel of 5 expert perfumers, both in a wet state and after drying.

The panel indicated, on a scale of values from 1 to 10, the intensity of the perceived odor for each sample, 10 corresponding to the most intense odor.

The results are given in the following table:

TABLE 1

Odor intensity of samples A and B for different textiles, on wet and dried linen

|  | Cotton | | Nylon ® | | Acrylic | | Mixture | |
| --- | --- | --- | --- | --- | --- | --- | --- | --- |
|  | wet | dry | wet | dry | wet | dry | wet | dry |
| Sample A | 9.5 | 10 | 10 | 9 | 10 | 9 | 10 | 8 |
| Sample B | 8 | 7.5 | 8 | 7 | 8 | 6.5 | 7.5 | 7.5 |

It clearly appears from this study that sample A and consequently 3-(4-tert-butyl-1-cyclohexen-1-yl)propanal is by far more tenacious and substantive than Lilial®. Similarly, the compound of the invention was unanimously judged more powerful on wet linen.

What is claimed is:

1. A method to confer, improve, enhance or modify the odor properties of a perfuming composition or a perfumed product, which method comprises adding a compound of formula

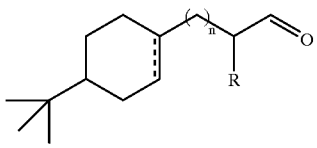

(I)

wherein either the dotted line indicates the location of a double bond, n is equal to 1 and R represents a hydrogen atom or a methyl radical, or the dotted line indicates the location of a single bond, n is equal to 0 and R represents a hydrogen atom, as perfuming ingredient to said composition or product.

2. A perfuming composition or a perfumed product containing as active ingredient a compound of formula (I) such as defined in claim 1.

3. A perfumed product according to claim 2, in the form of a perfume or cologne, a soap, a shower or bath gel, a shampoo or another hair-care product, a cosmetic preparation, a body deodorant or an air freshener, a detergent or fabric softener or a cleaning product.

4. A compound of formula (I) such as defined in claim 1, wherein the dotted line indicates the location of a double bond, n is equal to 1 and R represents a hydrogen atom or a methyl radical.

* * * * *

UNITED STATES PATENT AND TRADEMARK OFFICE
CERTIFICATE OF CORRECTION

PATENT NO. : 6,376,458 B1
DATED : April 23, 2002
INVENTOR(S) : Winter

It is certified that error appears in the above-identified patent and that said Letters Patent is hereby corrected as shown below:

Title page,
Item [73], Assignee, change "Firmewich" to -- Firmenich --.

Signed and Sealed this

Fifteenth Day of November, 2005

JON W. DUDAS
*Director of the United States Patent and Trademark Office*